United States Patent [19]

Fujii et al.

[11] Patent Number: 5,060,805
[45] Date of Patent: Oct. 29, 1991

[54] PHOTOELECTRON EMITTING MEMBER

[75] Inventors: Toshiaki Fujii, Kanagawa; Kazuhiko Sakamoto, Saitama, both of Japan

[73] Assignee: Ebara Research Co., Ltd., Fujisawa, Japan

[21] Appl. No.: 538,771

[22] Filed: Jun. 15, 1990

[30] Foreign Application Priority Data

Jun. 20, 1989 [JP] Japan .................. 1-155857
Jun. 12, 1990 [JP] Japan .................. 2-153335

[51] Int. Cl.$^5$ .............................................. B03B 1/00
[52] U.S. Cl. ........................................... 209/3; 55/2;
  55/102; 55/131; 55/138; 209/129
[58] Field of Search .............. 209/3, 8, 127.1, 129,
  209/571; 15/1.51; 55/2, 131, 102, 138;
  73/28.02, 28.04, 865.5; 250/423 P; 324/452,
  455

[56] References Cited

U.S. PATENT DOCUMENTS

| | | | |
|---|---|---|---|
| 4,205,969 | 6/1980 | Matsumoto | 55/138 X |
| 4,541,530 | 9/1985 | Kenny et al. | 209/571 |
| 4,685,569 | 8/1987 | Osaki et al. | 209/571 |
| 4,744,833 | 5/1988 | Cooper et al. | 15/1.51 |

FOREIGN PATENT DOCUMENTS

| | | |
|---|---|---|
| 61-178050 | 8/1986 | Japan . |
| 62-242838 | 10/1987 | Japan . |
| 62-244459 | 10/1987 | Japan . |
| 63-54959 | 3/1988 | Japan . |
| 63-77557 | 4/1988 | Japan . |
| 63-78471 | 4/1988 | Japan . |
| 63-97247 | 4/1988 | Japan . |
| 63-100955 | 5/1988 | Japan . |
| 63-100956 | 5/1988 | Japan . |
| 63-147565 | 6/1988 | Japan . |
| 63-147566 | 6/1988 | Japan . |
| 1-262953 | 10/1989 | Japan . |
| 1-262954 | 10/1989 | Japan . |
| 1-266864 | 10/1989 | Japan . |
| 2-8638 | 1/1990 | Japan . |
| 2-8639 | 1/1990 | Japan . |
| 2-10034 | 1/1990 | Japan . |
| 2-47536 | 2/1990 | Japan . |

OTHER PUBLICATIONS

The Sixth Technical and Research Forum of Aerosol Science, Aug. 1988, "Charging of Aerosol Particles by Photoelectric Effect", (English Abstract).
Man and His Ecosystem, Proceedings of the 8th World Clean Air Congress 1989 held at The Hague, 11-15 Sep. 1989.
Environmental Pollution, vol. 24, No. 5, (1989), 63-71, "Charging and Electrostatic Precipitation of Fine Particles by UV Irradiation".

Primary Examiner—Donald T. Hajec
Assistant Examiner—Joseph A. Kaufman
Attorney, Agent, or Firm—Oblon, Spivak, McClelland, Maier & Neustadt

[57] ABSTRACT

A photoelectron emitting member having a multiplex structure comprises a matrix and a protective film. The matrix being selected from the group consisting of elements, inorganic compounds, alloys, mixtures thereof and composites thereof which emit photoelectrons upon exposure to uv rays and other forms of radiation, the protective film comprising at least one material selected from the group consisting of metals, metallic compounds, plastics, polycyclic aromatic hydrocarbon, derivatives thereof or a mixture thereof which is film-forming and not thicker than 0.2 μm. The member can be used in a consistent way over a prolonged period as well as being capable of effective emission of photoelectrons. Fine particles electrically charged with photoelectrons which are emitted upon applying uv rays and/or other forms of radiation to the photoelectron emitting member, can be used in various applications such as (a) separation and classification of fine particles, as well as modifying their surfaces and controlling an electrically charged amount thereof; (b) the measurement of the concentration and size of fine particles in gases such as air and waste gases by using electrically charged fine particles; and (c) trapping and removal of charged fine particles to produce clean gases.

11 Claims, 1 Drawing Sheet

PHOTOELECTRON EMITTING MEMBER

BACKGROUND OF THE INVENTION

1. Field of the Invention

The present invention relates to a photoelectron emitting member providing a photoelectron effect.

Fine particles electrically charged with photoelectrons can be used in various applications such as (a) separation and classification of fine particles, as well as modifying their surfaces and controlling an electrically charged amount thereof; (b) the measurement of the concentration and size of fine particles in gases such as air and waste gases by using electrically charged fine particles; and (c) trapping and removal of charged fine particles to produce clean gases.

2. Description of the Prior Art

The present inventor has previously proposed many methods of electrically charging fine particles with photoelectrons that are emitted upon applying uv rays and/or other forms of radiation to a photoelectron emitting member and various applications of the thus formed photoelectron emitting member.

In the method of producing clean gases proposed by the present inventor, the following is particularly relevant to the present invention: Japanese Patent Public Disclosure (Laid-Open) Nos. 178050/1986 (corresponding to U.S. Pat. No. 4,750,917), 244459/1987, 77557/1988, 100955/1988 and 262954/1989.

With regard to the measurements, the following is proposed by the inventor: Japanese Patent Public Disclosure (Laid-Open) Nos. 242838/1987 and 47536/1990, and Japanese Patent Application No. 134781/1989.

With regard to the separation and classification, the following is proposed by the inventor: Japanese Patent Application No. 177198/1989.

Further, with regard to the conditions of electrically charging fine particles, the following is proposed by the inventor: Japanese Patent Application Nos. 120563/1989 and 120564/1989.

However, the conventional photoelectron emitting members were in a bulk-like (lump-like) form. Said members were limited in the amount of emitting photoelectrons they emitted and in the stability thereof, so there has been a need to modify such materials to provide for their improvement. The materials having a small work function which are capable of effective emission of photoelectrons are liable to deterioration and lack stability during prolonged operation.

SUMMARY OF THE INVENTION

It is therefore an object of the present invention to provide a photoelectron emitting member that can be used in a consistent way over a prolonged period as well as being capable of effective emission of photoelectrons.

Another object of the present invention is to provide a method of electrically charging fine particles using said improved photoelectron emitting member.

Another object of the present invention is to provide a method of various applications using said improved photoelectron emitting member.

Other objects and advantages of the present invention will become apparent to those skilled in the art from the following description and drawings.

DETAILED DESCRIPTION OF THE PREFERRED EMBODIMENTS

Figure 1:
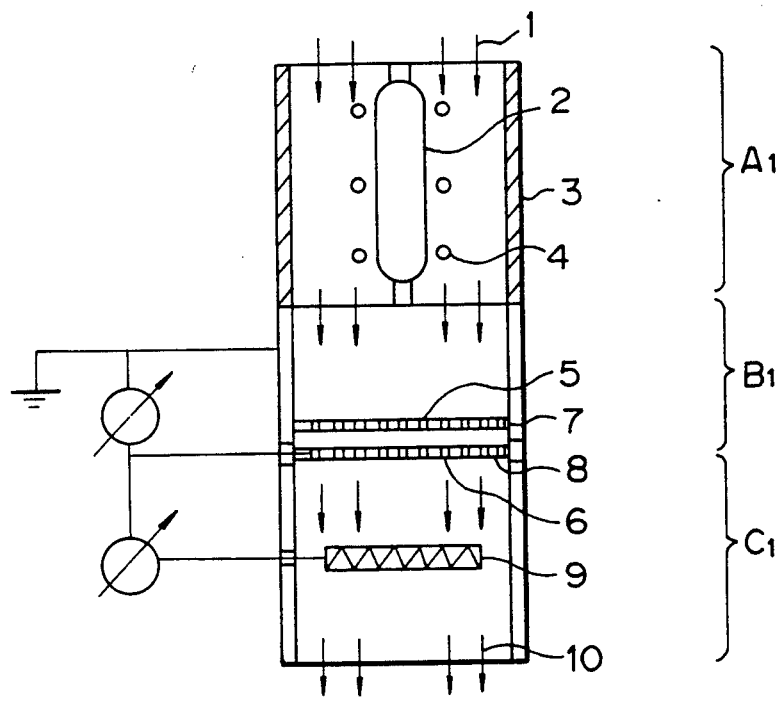
FIG. 1 is a schematic diagram of an apparatus for measuring fine particles suspended in air by a method according to an embodiment of the present invention.

The photoelectron emitting member to be used in the present invention has a multiplex structure composed of a matrix and a thin film serving as a protective film provided on said matrix. The matrix comprises elements, inorganic compounds, alloys, mixtures thereof or composites thereof which emit photoelectrons upon exposure to uv rays and/or other forms of radiation. The thin film comprises at least one material selected from the group consisting of metals, metallic compounds, plastics, polycyclic aromatic hydrocarbons and derivatives thereof which is film-forming and not thicker than 0.2 $\mu$m.

The matrix of the photoelectron emitting member may be made of any material that emits photoelectrons upon exposure to uv rays and/or other forms of radiation, and those materials which have a smaller photoelectric work function are preferred. From the viewpoints of efficiency and economy, the matrix is preferably made of either one of Ba, Sr, Ca, Y, Gd, La, Ce, Nd, Th, Pr, Be, Zr, Fe, Ni, Zn, Cu, Ag, Pt, Cd, Pb, Al, C, Mg, Au, In, Bi, Nb, Si, Ta, Ti, U, B, Eu, Sn and P, or compounds or alloys thereof. These materials may be used either on their own or as admixtures. Composites of these materials are also usable and an example is a physical composite such as an amalgam.

Compounds that can be used as matrix materials are oxide, borides and carbides. Exemplary oxides include $BaO$, $SrO$, $CaO$, $Y_2O_6$, $Gd_2O_3$, $Nd_2O_3$, $ThO_2$, $ZrO_2$, $Fe_2O_3$, $ZnO$, $CuO$, $Ag_2O$, $La_2O_3$, $PtO$, $PbO$, $Al_2O_3$, $MgO$, $In_2O_3$, $BiO$, $NbO$ and $BaO$; exemplary borides include $YB_6$, $CdB_6$, $LaB_6$, $NdB_5$, $CeB_6$, $EuB_6$, $PrB_6$ and $ZrB_2$; and exemplary carbides include $UC$, $ZrC$, $TaC$, $TiC$ and $NbC$.

Alloys that can be used as matrix materials are brass, bronze, phosphor bronze, alloys of Ag and Mg (2-20 wt % Mg), alloys of Cu and Be (1-10 wt % Be) and alloys of Ba and Al. Alloys of Ag-Mg, Cu-Be and Ba-Al systems are preferable.

The matrix materials described above may be used in various shapes including a flat plate, a pleated plate, a grid and a screen, with the surface being optionally roughened to provide asperities. Projections on the surface may have pointed or spherical tips. An optimum shape of the matrix can be determined from the results of preliminary testing in consideration of such factors as the size of equipment, its configuration, the type of photoelectron emitting member used, the manner in which an electric field is applied, operational efficiency and economy.

In the next place, the thin film which serves as a protective film on the matrix is described below.

The thin film may be made of any material that permits the passage of photoelectrons emitted from the matrix and that protects the surface of the matrix. The use of electroconductive material is effective and hence preferred in most cases. Such conductive materials may be coated or deposited as a thin film by an appropriate method, such as ion plating, sputtering, evaporation, CVD (chemical vapor deposition), forming an oxide layer on the surface of the conductive material by heat treatment, or forming a membrane by treating the conductive material with a chemical. These methods may be appropriately employed for the specific case of interest.

Exemplary conductive materials include Au, Ag, Al, Pb, Ti and Ni, which may be used as appropriate. Also usable are TiN, TiCN, TiAlN, HfN, ZrN, CrN, TaC, TiC, plastics, polycyclic aromatic hydrocarbons and derivatives thereof. An exemplary plastic material is an epoxy resin, and an exemplary polycyclic aromatic hydrocarbon is benzpyrene.

The thickness of the thin film should be such that it is thin enough to permit the passage of photoelectrons emitted from the matrix but thick enough to protect the surface of the matrix. The thin film usually has a thickness of up to 0.2 $\mu$m, preferably up to 0.05 $\mu$m, and an optimum thickness can be determined from the results of preliminary testing in consideration of the material of which the matrix of the photoelectron emitting member and the thin film provided on it is to be made, the shape in which said member is to be used, the manner in which an electric field is to be applied, and the operational efficiency.

In accordance with the present invention, the thin film provided on the matrix made of a material having a small work function protects the matrix from the adverse effect of the ambient atmosphere (air in the case being considered), whereby the emission of photoelectrons is stabilized and sustained for a prolonged period.

The application of uv rays and/or other forms of radiation to the photoelectron emitting member is now described below. Any source of uv rays may be used as long as the photoelectron emitting member will emit photoelectrons upon irradiation with uv rays, and exemplary sources are a mercury lamp, a hydrogen discharge tube, a xenon discharge tube and a Lyman discharge tube. Other forms of radiation may be employed as long as the photoelectron emitting member will emit photoelectrons upon exposure to such radiation, and examples are $\alpha$-rays, $\beta$-rays and $\gamma$-rays. Suitable radiation sources include radioisotopes such as cobalt 60, cesium 137 and strontium 90, radioactive wastes produced in nuclear reactors, and radioactive materials prepared by processing such radioactive wastes in an appropriate way. The choice of a suitable uv or radiation source depends on such factors as the shape of a charging section used, the field of its application, the required precision of measurement, and economy.

Effective emission of photoelectrons from the photoelectron emitting member is insured by applying uv rays and/or other forms of radiation to the photoelectron emitting member in an electric field. The choice of an appropriate method for forming an electric field depends on such factors as the shape of a charging section used, its construction, the field of its application and the effect desired. The strength of electric field to be applied can be properly determined in consideration of such factors as concentration of concomitant water and the type of photoelectron emitting member used, and detailed information can be found in the specification of another commonly assigned invention. As a guide, an electric field having an intensity of from 2 volts/cm to 2 kilovolts/cm may be applied.

Electrodes that are used in applying an electric field may be made of any material in any construction commonly employed in ordinary charging devices. For instance, tungsten wires or rods may be used as electrodes.

Measurement of fine particle suspended in the air by the method of the present invention is specifically described below with reference to FIGS. 1 and 2. FIG. 1 shows schematically a measuring apparatus that uses classifying plates for classifying charged fine particles and an electrometer as a detector. Air 1 containing suspended fine particles that is preliminarily cleaned of coarse particles larger than 10 $\mu$m by means of a suitable device such as an impactor (not shown) is introduced into the apparatus through an intake port. In a charging section $A_1$, the introduced fine particles are electrically charged with photoelectrons emitted from a photoelectron emitting surface 3 upon irradiation with uv rays from a uv source 2.

The charging section $A_1$ is chiefly composed of the uv lamp 2, the photoelectron emitting member 3 and electrodes 4. In the charging section $A_1$, an electric field is formed between the photoelectron emitting member 3 and each of the electrodes 4, so that photoelectrons will be effectively emitted from the surface of the member 3 upon illumination with the uv lamp 2. The fine particles in the air 1 introduced through the intake port are electrically charged by the action of the emitted photoelectrons.

The charged fine particles are classified in a classifying section $B_1$. The classifying section $B_1$ has a compact and simple construction for classifying the charged fine particles and performs the function of classifying them in response to the charge in the voltage supplied to the classifying plates.

The operation of the classifying plates 7 and 8 having pores 5 and 6 is described below. An electric field as produced from a power source is formed between these two classifying plates 7 and 8. Let the total number of charged fine particles in the classifying section $B_1$ be written as $b_1$. First, a weak electric field $a_1$ is formed between the plates 7 and 8, whereupon the charged particles $b_2$ that are small enough to be subjected to the action of the weak electric field are trapped on the classifying plates. As a result, the amount of electric charge $d_1$ on the remaining coarse particles ($b_1 - b_2$) is measured in the detecting section $C_1$ composed of an electrometer 9 positioned downstream of the classifying plates, whereby the concentration of the coarse particles is determined.

In the next place, an electric field $a_2$ stronger than $a_1$ is formed between the classifying plates 7 and 8, whereupon the charged particles $b_3$ that are coarser than $b_2$ are subjected to the action of that strong field and are trapped on the classifying plates. As a result, the amount of electric charge on the remaining coarse particles ($b_1 - b_3$) is measured with the electrometer 9. In subsequent steps, the electric field applied to the classifying plates is properly changed to perform similar measurements of the electric charge on the charged particles.

Thus, the step of classification as combined with the measurement of the concentration of fine particles will provide information on the particle size distribution of the fine particles suspended in the air 1 at the intake port, as well as the concentrations of the particles in respective size ranges.

In section $C_1$, the charged fine particles classified in the classifying section $B_1$ are detected with the electrometer 9. The electrometer 9 may be of any type that is capable of measuring the amount of charge on the classified particles to provide information on the concentration of classified particles. Shown by 10 is an air outlet.

The photoelectron emitting member 3 used in the apparatus under consideration comprises a ZrC matrix coated with an Au film having a thickness of 0.01 μm.

The structure of the photoelectron emitting member 3 which is the characterizing portion of the present invention is described below with reference to FIG. 2, in which the photoelectron emitting member is partly shown in cross section. The photoelectron emitting member 3 is composed of a matrix 11 typically made of a material having a small photoelectric work function, and a thin film 12 on the matrix 11 which serves as a protective film for it.

As already mentioned hereinabove, the matrix 11 of the photoelectron emitting member 3 may be made of any material that is capable of emitting photoelectrons upon exposure to uv rays and/or other forms of radiation. Materials having a smaller photoelectric work function are preferred. The thin film 12 serving as the protective film on the matrix 11 may also be made of any material that permits the passage of photoelectrons emitted from the matrix and that protects its surface.

Figure 2:
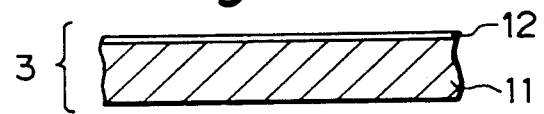
FIG. 2 is a partial cross section of the photoelectron emitting member used in the apparatus shown in FIG. 1.

In the case shown in FIGS. 1 and 2, the photoelectron emitting member 3 is of a dual structure consisting of the matrix 11 and the thin film 12 provided on it. Needless to say, the photoelectron emitting member 3 may be of a triplex structure in which either the matrix 11 or the thin film 12 provided on it is composed of more than one layer. If desired, a multiplex structure can be fabricated by further increasing the number of layers of which the matrix 11 or the thin film 12 is composed.

EXAMPLES

The following examples are provided for the purpose of further illustrating the present invention but are in no way to be taken as limiting.

EXAMPLE 1

A thin gold or silver film was vapor-deposited on the surface of the matrix of a photoelectron emitting member, and the amount of photoelectrons emitted into the atmosphere was measured with an open-air, uv excited photoelectron analyzer. The matrix was made of ZrC. The results obtained with ZrC shown below, in which the data refers to the amount of photoelectrons emitted per second and raised to the one-half power, Y.

TABLE 1

| | Vapor-deposited film | | | | | |
|---|---|---|---|---|---|---|
| | | Au (μm) | | | Ag (μm) | |
| Matrix | None | 1.0 | 0.05 | 0.01 | 1.0 | 0.05 | 0.01 |
| ZrC | 26.5 | 17.0 | 28.0 | 30.5 | 18.5 | 29.5 | 33.5 |

Y of Au and Ag in a bulk-like form is as follows:

Au:11.0, Ag:13.5

EXAMPLE 2

Figure 3:
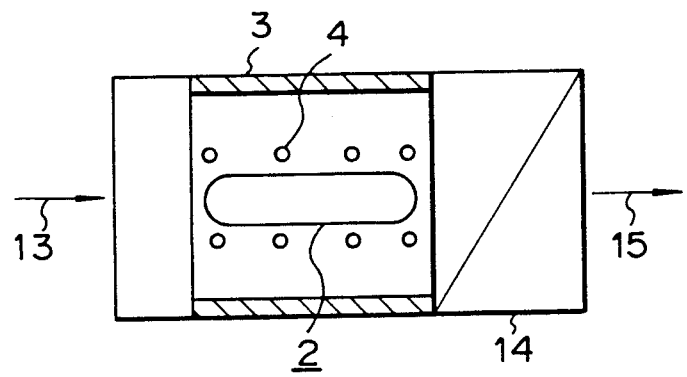
FIG. 3 is a schematic diagram of the air cleaner used in Example 2 and Comparative Example.

The performance of an air cleaner having the construction shown in FIG. 3 was checked with a particle measuring apparatus, with cigarette smoke being supplied at a rate of 5 l/min after dilution with air. The photoelectron emitting member used comprised a ZrC matrix on which was vapor-deposited a gold film in a thickness of 0.01 μm as in Example 1. A low-pressure mercury lamp was used as a uv source. An electric field of 50 volts/cm was applied between the mercury lamp and each electrode. As shown in FIG. 3, the air cleaner consisted of the photoelectron emitting member 3, mercury lamp 2', electrodes 4 and a dust collector plate 14. The cigarette smoke was admitted through an inlet 13 and discharged from an outlet 15. The smoke was found to contain $5.3 \times 10^6$ particles per liter at the inlet, and only 210 particles per liter at the outlet. The test was continuously operated for one month and no change in its efficiency was found.

COMPARATIVE EXAMPLE

The test procedure of Example 1 was repeated except that the photoelectron emitting member was solely composed of ZrC. The cigarette smoke was found to contain $5.2 \times 10^6$ particles per liter at the inlet, and it still contained as many as $15.3 \times 10^3$ particles at the outlet. The test was continued and $18.05 \times 10^4$ particles per liter were found after three days with $38.11 \times 10^4$ particles per liter at the outlet.

The present invention offers the following advantages.

1. The photoelectron emitting member is composed of a matrix that is made of a material having a small work function (which is responsible for emitting photoelectrons) and a thin film formed on the matrix (which serves to protect the photoelectron emitting matrix) and, hence,
   (i) the use of a matrix material that has a small enough work function to provide enhanced emission of photoelectrons insures improved efficiency, and the protected matrix surface permits consistent operation for a prolonged time;
   (ii) the enhanced and consistent emission of photoelectrons leads to effective charging of fine particles (i.e., efficient charging can be performed for a prolonged period); and
   (iii) the effective charging of fine particles enables the use of a small (compact) apparatus and contributes to a larger throughput in processing.
2. Because of the advantages described above, the following benefits are achieved in various fields of application:
   (i) In measurement applications,
      a. the measurement precision is improved and consistent results are attained for a prolonged period;
      b. a particularly great improvement is achieved in the precise measurement of superfine (<0.1 μm) particles;
   (ii) In applications where clean gases or liquids are to be obtained,
      a. improved performance is attained for a prolonged period;
      b. the apparatus size is reduced and the throughput of processing is increased;
   (iii) In applications where particle separation, classification or other control is to be performed,
      a. improved performance is attained for a prolonged period;
      b. the apparatus size is reduced and the throughput of processing is increased; and c. a particularly great improvement is achieved in the efficiency of processing superfine (<0.1 μm) particles.

What is claimed is:

1. A photoelectron emitting member having a multiplex structure comprising a matrix and a conductive, protective film disposed over said matrix, said matrix being selected from the group consisting of elements, inorganic compounds, alloys, mixtures thereof and composites thereof which emit photoelectrons upon exposure to uv rays and other forms of radiation, said conductive, protective film comprising at least one material selected from the group consisting of metals, metallic compounds, plastics and polycyclic aromatic hydrocarbons and derivatives thereof which is film-forming, said conductive, protective film being not thicker than 0.2 μm.

2. A photoelectron emitting member according to claim 1 wherein at least part of said matrix is made of materials having a small photoelectric work function.

3. A photoelectron emitting member according to claim 1 wherein said conductive protective thin film is not thicker than 0.05 μm.

4. A photoelectron emitting member according to claim 1 wherein said matrix is made of at least one material selected from the group consisting of Ba, Sr, Ca, Y, Gd, La, Ce, Nd, Th, Pr, Be, Zr, Fe, Ni, Zn, Cu, Ag, Pt, Cd, Pb, Al, C, Mg, Au, In, Bi, Nb, Si, Ta, Ti, U, B, Eu, Sn, P and compounds thereof.

5. A photoelectron emitting member according to claim 1 wherein said matrix is made of an alloy, mixture or composite of at least two members selected from the group consisting of Ba, Sr, Ca, Y, Gd, La, Ce, Nd, Th, Pr, Be, Zr, Fe, Ni, Zn, Cu, Ag, Pt, Cd, Pb, Al, C, Mg, Au, In, Be, Nb, Si, Ta, Ti, U, B, Eu, Sn, P and compounds thereof.

6. A photoelectron emitting member according to claim 1 wherein said conductive protective film is made of at least one material selected from the group consisting of Au, Ag, Al, Pb, Ti, Ni, TiN, TiCN, TiAlN, HfN, ZrN, CrN, TaC, TiC, plastics and polycyclic aromatic hydrocarbons and derivatives thereof.

7. A method of electrically charging fine particles in an electric field comprising:

providing a photoelectron emitting member having a multiplex structure comprising a matrix and a conductive, protective film disposed over said matrix, said matrix being selected from the group consisting of elements, inorganic compounds, alloys, mixtures thereof and composites thereof which emit photoelectrons upon exposure to uv rays and other forms of radiation, said conductive, protective film comprising at least one material selected from the group consisting of metals, metallic compounds, plastics, and polycyclic aromatic hydrocarbons and derivatives thereof which is film-forming, said conductive, protective film being not thicker than 0.2 μm;

providing a radiation source, spaced apart from said photoelectron emitting member, for irradiating said photoelectron emitting member with radiation causing the emission of photoelectrons;

providing at least one electrode proximate said radiation source;

flowing a gas stream containing fine particles between said photoelectron emitting member and said radiation source;

irradiating said photoelectron emitting member with radiation from said radiation source while said gas stream flows therebetween to cause the emission of photoelectrons from said photoelectron emitting member, while simultaneously applying an electric field between said photoelectron emitting member and said at least one electrode, to charge said fine particles in said gas stream.

8. The method according to claim 7 wherein the electric field has an intensity of from 2 volts/cm to 2 kilovolts/cm.

9. The method according to claim 7, further comprising treating said charged fine particles with a classifying means for sorting said particles by size.

10. The method according to claim 7, further comprising treating said charged fine particles with a classifying means for sorting said particles by size; and then treating said sorted particles with a detector to determine the concentration thereof.

11. The method according to claim 7, further comprising trapping said charged fine particles in a collector.

* * * * *